(12) United States Patent
Beckers et al.

(10) Patent No.: US 10,923,099 B2
(45) Date of Patent: Feb. 16, 2021

(54) ACOUSTICAL LENS AND ULTRASOUND TRANSDUCER PROBE

(71) Applicant: KONINKLIJKE PHILIPS N.V., Eindhoven (NL)

(72) Inventors: Lucas Johannes Anna Maria Beckers, Veldhoven (NL); Peter Dirksen, Valkenswaard (NL); Nico Maris Adriaan de Wild, Eindhoven (NL); Franciscus Johannes Gerardus Hakkens, Eersel (NL)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 15/309,493

(22) PCT Filed: Apr. 30, 2015

(86) PCT No.: PCT/EP2015/059439
§ 371 (c)(1),
(2) Date: Nov. 8, 2016

(87) PCT Pub. No.: WO2015/173027
PCT Pub. Date: Nov. 19, 2015

(65) Prior Publication Data
US 2017/0154619 A1 Jun. 1, 2017

(30) Foreign Application Priority Data

May 14, 2014 (EP) .................................... 14168372

(51) Int. Cl.
*G01K 11/30* (2006.01)
*G10K 11/30* (2006.01)
(Continued)

(52) U.S. Cl.
CPC ............ *G10K 11/30* (2013.01); *A61B 8/4281* (2013.01); *A61B 8/4444* (2013.01);
(Continued)

(58) Field of Classification Search
CPC ......... G10K 11/30; A61B 8/00; A61B 8/4281; A61B 8/4444; A61B 8/4483; A61B 8/483; G01N 29/24; G01N 29/2456
See application file for complete search history.

(56) References Cited

U.S. PATENT DOCUMENTS 4,659,956 A 4/1987 Trzaskos et al.
4,699,150 A * 10/1987 Kawabuchi ............ G10K 11/30
600/446
(Continued)

FOREIGN PATENT DOCUMENTS

EP 2289419 A1 * 3/2011 ........... A61B 8/4455
EP 2289419 A1 3/2011
(Continued)

*Primary Examiner* — Hovhannes Baghdasaryan
*Assistant Examiner* — Amie M Ndure

(57) ABSTRACT

An acoustical lens (20) for an ultrasound probe (14) is disclosed. The acoustical lens comprises an inner surface (26) for facing an emission surface (46) of an ultrasound transducer (40) and for receiving ultrasound waves from the ultrasound transducer. The acoustical lens further comprises an outer surface (24) for emitting the ultrasound waves received at the inner surface, wherein the inner surface is formed as a convexly curved surface and wherein at least one recess (34) is associated to an edge of the inner surface for capturing mold material.

19 Claims, 4 Drawing Sheets

(51) Int. Cl.
*A61B 8/00* (2006.01)
*G01N 29/24* (2006.01)
*A61B 8/08* (2006.01)

(52) U.S. Cl.
CPC ....... *A61B 8/4483* (2013.01); *G01N 29/2456* (2013.01); *A61B 8/483* (2013.01)

(56) References Cited

U.S. PATENT DOCUMENTS

| | | | | |
|---|---|---|---|---|
| 5,465,724 | A | * | 11/1995 | Sliwa, Jr. ................. A61B 8/12 600/459 |
| 5,562,096 | A | * | 10/1996 | Hossack ................... A61B 8/12 600/446 |
| 5,976,091 | A | | 11/1999 | Hanafy |
| 7,888,847 | B2 | | 2/2011 | Dietz et al. |
| 8,189,850 | B2 | * | 5/2012 | Ono ....................... B06B 1/0633 29/594 |
| 2003/0142413 | A1 | * | 7/2003 | McLean ................ A61C 19/004 359/708 |
| 2009/0299193 | A1 | * | 12/2009 | Haftman .............. G10K 11/355 600/459 |

FOREIGN PATENT DOCUMENTS

| | | | | |
|---|---|---|---|---|
| EP | | 2308397 A1 | 4/2011 | |
| JP | | 9075345 A | 3/1997 | |
| JP | | 2004105741 A | 4/2004 | |
| WO | | 2010031192 A1 | 3/2010 | |
| WO | | 2013046080 A1 | 4/2013 | |
| WO | WO-2015177631 A2 | * | 11/2015 | ............. G01V 1/155 |

* cited by examiner

ACOUSTICAL LENS AND ULTRASOUND TRANSDUCER PROBE

This application is the U.S. National Phase application under 35 U.S.C. § 371 of International Application No. PCT/EP2015/059439, filed on Apr. 30, 2015, which claims the benefit of European Application Serial No. 14168372.2, filed May 14, 2014. These applications are hereby incorporated by reference herein.

FIELD OF THE INVENTION

The present invention relates to an acoustical lens for an ultrasound probe including an ultrasound transducer for emitting ultrasound waves. The present invention further relates to an ultrasound transducer probe comprising an ultrasound transducer for emitting ultrasound waves.

BACKGROUND OF THE INVENTION

Ultrasound probes are typically formed by an ultrasound transducer comprising one or more transducer elements and an acoustical lens for providing the ultrasound waves from the transducer to an outer concave surface which can be brought into contact e.g. with a human body for an ultrasound examination. The ultrasound transducers are usually molded with a connection mold or a glue to the acoustical lens in order to provide a good acoustical contact between the transducer elements and the outer surface of the acoustical lens, however, the connection mold usually comprise air bubbles while mounting the ultrasound transducer to the acoustical lens, which lead to acoustical reflections and an attenuation of the acoustical waves emitted from the transducer so that the efficiency of the ultrasound probe is reduced.

Further, the typically used connection molds or glues are susceptible for fluid incrust so that the acoustical stack, in particular the connection mold has to be protected against moisture from the outside of the acoustical lens.

In order to reduce the acoustical reflections between the transducer and the acoustical lens WO 2013/046080 proposes to scatter the acoustical waves in different spatial directions by means of a scattering surface, however, air bubbles included in the connection mold may still attenuate the emitted ultrasound waves.

U.S. Pat. No. 4,699,150 A discloses an ultrasonic transducer for medical diagnostic examination which comprises a transducer element having one surface through which acoustic waves are emitted, an acoustic impedance matcher, and a contact member brought into contact with an object being examined and formed on the one surface of the ultrasonic transducer element.

U.S. Pat. No. 4,659,956 A discloses a compound focus ultrasonic transducer for non-destructive evaluation and material characterization applications comprising a piezoelectric ceramic element having a first radius of curvature and a combination lens and a cover layer on its front having a second radius of curvature which is less than the first radius of the piezoelectric ceramic element.

Further ultrasound transducers are known from JP 2004 105741 A, U.S. Pat. No. 5,976,091 A, and EP 2 289 419 A1.

SUMMARY OF THE INVENTION

It is an object of the present invention to provide an acoustical lens for an ultrasound probe and an ultrasound probe including an acoustical lens having an improved ultrasound emission.

In a first aspect of the present invention, an acoustical lens for an ultrasound probe is provided, comprising:
an inner surface for facing an emission surface of an ultrasound transducer and for receiving ultrasound waves from the ultrasound transducer,
an outer surface for emitting the ultrasound waves received at the inner surface,
wherein the inner surface is formed as a convexly curved surface, and
wherein at least one recess is associated to an edge of the inner surface for capturing mold material.

In a further aspect of the present invention, an ultrasound transducer probe is provided, comprising:
an ultrasound transducer including an emission surface for emitting ultrasound waves, and
an acoustical lens having an inner surface for facing the emission surface of the ultrasound transducer and for receiving the ultrasound waves from the emission surface and an outer surface for emitting the ultrasound waves received at the inner surface, wherein the inner surface is formed as a convexly curved surface, and wherein at least one recess is associated to an edge of the inner surface for capturing mold material.

Preferred embodiments of the invention are defined in the dependent claims. It shall be understood that the claimed ultrasound transducer probe has similar and/or identical preferred embodiments as the claimed acoustical lens and as defined in the dependent claims.

The present invention is based on the idea to achieve an air bubble free mold connection between the emission surface of the ultrasound transducer and the inner surface of the acoustical lens to improve the acoustical connection between the emission surface and the inner surface in the main emission direction of the ultrasound waves. Since the inner surface is formed as a convexly curved surface, the thickness of the connection mold layer is reduced in a central portion which corresponds to the main direction of the ultrasound waves. While connecting the ultrasound transducer to the inner surface, the connection mold is moved or driven by the convexly curved surface to peripheral parts of the inner surface so that the included air bubbles are also driven to the peripheral part and the central part of the connection mold which corresponds to the main direction of the ultrasound waves is air bubble free and the thickness of the mold is reduced compared to the peripheral parts. Further, the recess can serve as a cavity for capturing excessive connection mold when the emission surface is brought into contact with the inner surface and to capture the air bubbles and the voids within the contact mold. Hence, the acoustical reflections at the air bubbles in the main direction of the ultrasound waves and the corresponding attenuation of the ultrasound waves can be reduced so that the ultrasound wave emission efficiency is increased.

According to a preferred embodiment, the inner surface is formed as a single convexly curved portion. This is a possibility to reduce the thickness of the contact mold at a central portion of the inner surface corresponding to the main direction of the ultrasound waves so that the attenuation of the ultrasound waves in the main emission direction is reduced and the efficiency of the ultrasound wave emission is improved. Further, the single convexly curved portion can multiple reflections so that the main direction of the ultrasound waves induced by the ultrasound transducer is not disturbed.

In a preferred embodiment, the recess has a concave shape. This is a possibility to provide the recess within the acoustical lens with low technical effort.

In a preferred embodiment, the recess is formed as a notch surrounding the inner surface at least partially. This is a possibility to capture the air bubbles in the connection mold and to receive the excessive material with high efficiency since the excessive material can be pushed to the sides of the convexly curved surface by pressing the emission surface to the inner surface.

In a preferred embodiment, side walls are associated to the inner surface forming a cavity together with the inner surface for receiving the ultrasound transducer. This is a possibility to form a reliable connection between the ultrasound transducer and the acoustical lens, since the acoustical lens forms a cavity for receiving the ultrasound transducer and supports the ultrasound transducer laterally.

In a preferred embodiment, the recess is formed as a notch separating the inner surface from inner surfaces of the side walls. This is a possibility to provide a cavity for excessive material of the connection mold which can receive the excessive connection mold easily, since the recess is formed as an edge between the side walls and the inner surface.

In a preferred embodiment, the inner surface is covered by a coating forming a moisture barrier. This is a possibility to protect the connection mold against moisture so that the probe can be used in a wet environment and the reliability of the mechanical connection between the ultrasound transducer and the acoustical lens is improved.

In a preferred embodiment, the inner surfaces of the side wall and a surface of the recess are covered by a coating forming the moisture barrier. This is a possibility to further improve the reliability of the mechanical connection, since the connection mold is entirely surrounded and protected against moisture.

In a preferred embodiment, the coating is formed as a metal layer. This is a possibility to provide the moisture barrier with high efficiency and low technical effort.

In a preferred embodiment, the recess is formed as a blind hole or a blind notch.

In a preferred embodiment of the ultrasound probe, the emission surface is connected to an inner surface by means of a connection mold. This is a possibility to improve the mechanical connection between the ultrasound transducer and the acoustical lens and to improve the efficiency of the ultrasound wave emission, since the connection mold reduces the ultrasound wave reflection at the inner surface of the acoustical lens.

In a preferred embodiment, the emission surface is a planar surface. This is a possibility to manufacture the ultrasound transducer with low technical effort, since the transducer can be formed e.g. as a capacitive micromachined ultrasound transducer on a silicon wafer and connected to the acoustical lens with an improved ultrasound wave emission efficiency.

As mentioned above, the present invention can reduce the reflection of the ultrasound waves at the interface between the emission surface and the inner surface of the acoustical lens, since air bubbles can be driven from a middle portion of the inner surface to a peripheral side portion of the inner surface when the emission surface and the inner surface are connected by means of a connection mold and the two surfaces are pressed to each other. Since the air bubbles are removed from the central portion of the emission surface, which is the main emission direction of the ultrasound waves and since the thickness of the connection mold can be reduced at this central portion, the reflections and the attenuation of the ultrasound waves is reduced and the efficiency of the ultrasound wave emission is improved.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
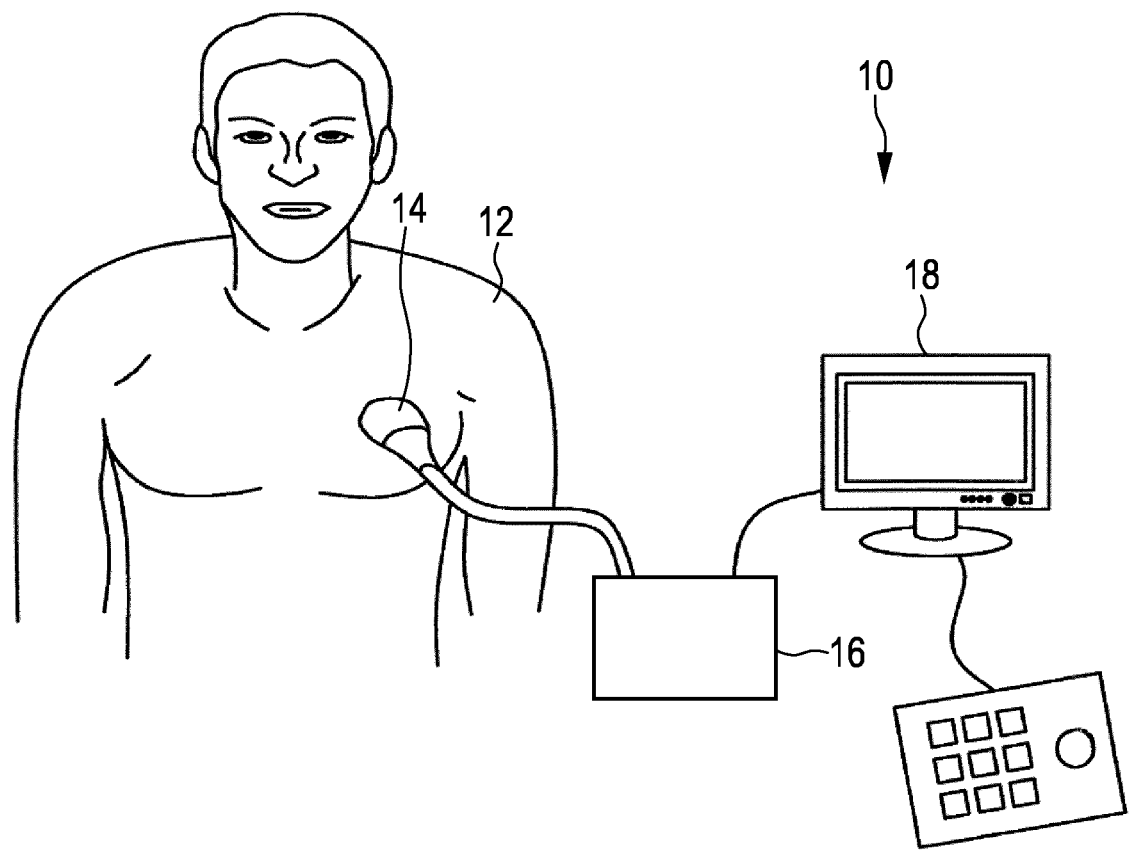
FIG. 1 shows a schematic representation of an ultrasound imaging system in use to scan a volume of a patient's body.

FIG. 1 shows a schematic illustration of an ultrasound system 10 according to an embodiment, in particular a medical three-dimensional (3D) ultrasound imaging system. The ultrasound imaging system 10 is applied to inspect the volume of an anatomical side, in particular an anatomical side of a patient 12. The ultrasound system comprises an ultrasound probe 14 having at least one ultrasound transducer, in particular an ultrasound transducer array having a multitude of transducer elements for transmitting and/or receiving ultrasound waves. The ultrasound probe 14 comprises an acoustical lens connected to the ultrasound transducer forming a contact surface of the ultrasound probe 14 for connecting the ultrasound probe 14 to the patient 12.

Further, the ultrasound system 10 may comprise a controlling unit 16 that controls the provision of a 3D image via the ultrasound system 10. The controlling unit 16 controls not only the acquisition of data via the transducer array of the ultrasound probe 14, but also signal and image processing that form the 3D images out of the echoes of the ultrasound beams received by the transducer array of the ultrasound probe.

The ultrasound system may further comprise a display 18 for displaying the 3D images to the user and may comprise an input device including keys or a keyboards as a user interface.

Figure 2:
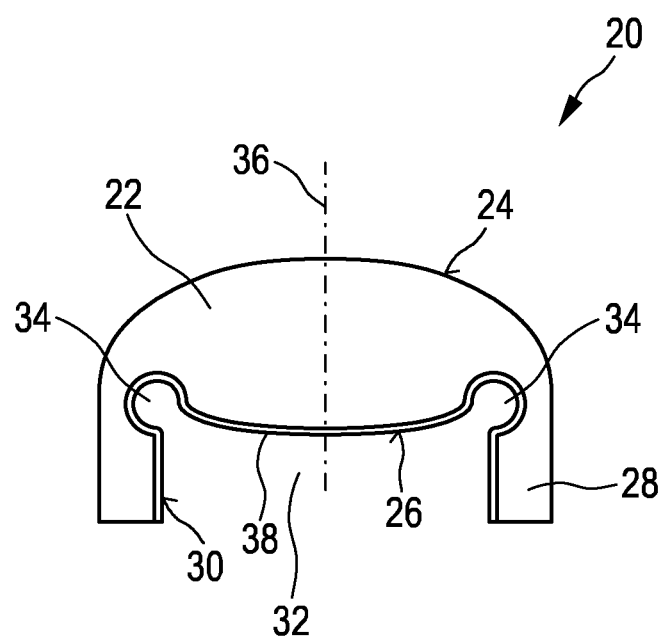
FIG. 2 shows a schematic cross sectional view of an acoustical lens for an ultrasound probe.

FIG. 2 shows a schematic sectional view of an acoustical lens for the ultrasound probe 14 generally denoted by 20. The acoustical lens 20 comprises a main body 22 that may be formed of a thermoplastic elastomer, which is capable of submitting ultrasound waves. The main body comprises an outer surface 24 and an inner surface 26. The inner surface 26 is generally adapted to face an emission surface of an ultrasound transducer and for receiving ultrasound waves from the ultrasound transducer. The outer surface 24 is generally adapted to emit the ultrasound waves received at the inner surface and submitted via the main body 22. The outer surface 24 is also adapted to receive ultrasound waves and to provide the received ultrasound waves to the ultrasound transducer. The outer surface 24 has a convexly curved shape in order to emit the ultrasound waves correspondingly in a radial direction. The inner surface 26 is formed as a convexly curved surface having a curvature opposite to the curvature of the outer surface.

The main body 22 further comprises one or a plurality of side walls 28 extending in this sectional view in a direction opposite to the outer surface 24. The side walls 28 comprise an inner surface 30, which form a cavity 32 for receiving the ultrasound transducer as described in the following. The main body 22 is formed as an integral part in one piece.

Between the inner surface 26 and the inner surface 30 of the side walls 28, one or more recesses 34 are formed for capturing excessive connection mold which is used for connecting the ultrasound transducer to the acoustical lens 20 as described in the following. The recesses 34 may be formed as separate recesses between the inner surface 26 and the inner surface 30 of the side walls 28 or may be a continuous notch at the edge between the inner surface 26 and the inner surface 30 of the side walls 28. The recess 34 is formed as a cavity or a blind hole or blind notch.

The main body 22 may have a circular shape and is symmetrical to an axis of symmetry 36. The sectional view of FIG. 2 has to be understood that the inner surface 26 and the outer surface 24 are both two dimensional planes which expand orthogonally from the paper plane. Thereby, both surfaces 24, 26 are arranged at opposite sides of the main body 22. The side walls 28 are preferably formed as a cylindrical portion extending coaxially in a direction of the axis of symmetry 36.

The inner surface 26, the inner surfaces 30 of the side walls 28 and an inner surface of the cavity 34 are covered by a moisture barrier layer 38. The moisture barrier layer 38 is provided to protect the cavity 32 in general against moisture from the outside. The moisture barrier layer 38 is preferably formed as a metal layer.

The main body 22 is preferably formed by the polyether block amide PEBAX 2533, which is a thermoplastic elastomer, made of flexible polyether and writhed polyamide.

Figure 3:
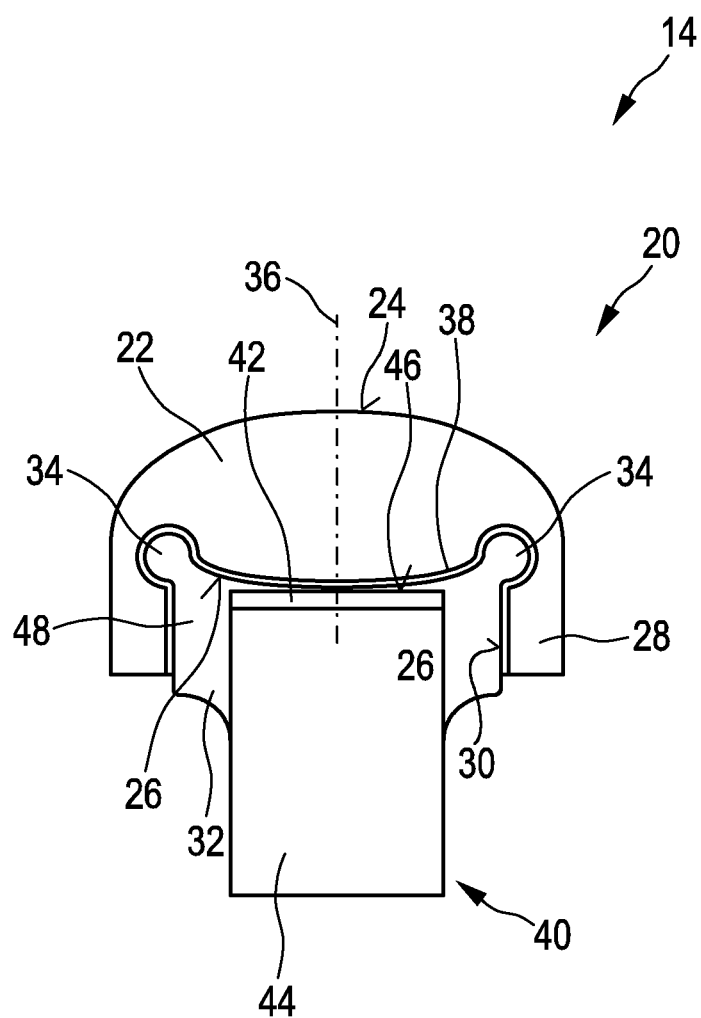
FIG. 3 shows a schematic cross sectional view of an ultrasound probe including an acoustical lens shown in FIG. 2.

FIG. 3 shows a schematic sectional view of the ultrasound probe 14 comprising the acoustical lens 20 and an ultrasound transducer which is generally denoted by 40. The ultrasound transducer 40 comprises an ultrasound transducer element 42 or an ultrasound transducer array 42 for transmitting and/or receiving ultrasound waves. The ultrasound transducer element 42 or the ultrasound transducer array 42 is formed as a ceramic micromachined ultrasound transducer on wafer level and attached to a support portion 44, which is provided for mechanically supporting the transducer element or array 42 and for electrically connecting the transducer elements 42. The support portion 44 may be a flexible mount structure having an underfill for the transducer element 42 or the transducer array 42. The transducer element 42 or the transducer array 42 comprises an emission surface 46 for emitting and/or receiving the ultrasound waves.

The ultrasound transducer 40 is disposed at least partially within the cavity 32 and attached to the inner surfaces 26, 30 of the cavity 32 by means of a connection mold or a glue 48. The glue 48 is formed as a PDMS (Polydimethylsiloxan) or a Polybutadine in order to fix the ultrasound transducer 40 in the cavity 32 and to form a good acoustic connection to the inner surface 26.

The ultrasound transducer 40 is disposed within the cavity 32 so that the emission surface 46 faces the inner surface 26 and the side walls 28 support the ultrasound transducer 40 laterally. In this position, the ultrasound waves emitted from the emission surface 46 can be provided to the inner surface 26 and further submitted to the outer surface 24 via the main body 22. Due to the convexly curved shape of the inner surface 26, a central portion of the emission surface 46, which forms the main emission direction of the ultrasound transducer element 42 or the transducer array 42 along the axis of symmetry 36, is in close contact to the inner surface 26 so that the attenuation and the reflections at this central portion are reduced. During the manufacturing process, an ultrasound transducer 40 is pressed into the cavity 32, so that the glue 48 is driven from the central portion of the emission surface 46 to the peripheral portion and also avoids or air bubbles included in the mold 48 are driven to the peripheral portion as described in the following.

The moisture barrier layer 38 protects the glue 32, which is hydrophilic, from the outside, so that the ultrasound probe 14 can be used in wet environments without damaging the glue 48 by intruding moisture.

The recesses 34 serve as a cavity for excessive glue 48, which is pressed during the manufacturing process to the sides into the recesses 34 so that the emission surface 46 can be brought into close contact to the inner surface 26.

FIGS. 4a-d show process steps to manufacture the ultrasound probe 14 including the acoustical lens 20 and the ultrasound transducer 40. In other words, FIG. 4a-d show process steps to connect the ultrasound transducer 40 into the cavity 32 of the acoustical lens 20.

The ultrasound transducer 40 comprises the transducer element 42 or the transducer array 42 attached to the support portion 44 and having the emission surface 46 as described above. The transducer elements 42 can be the capacitive micromachined ultrasound transducers (CMUTs) manufactured by the available microfabrication techniques, such as sacrificial layer etching or wafer-bonding. The transducer elements 42 can be also piezoelectric based ultrasound transducers (PZTs).

Figure 4:
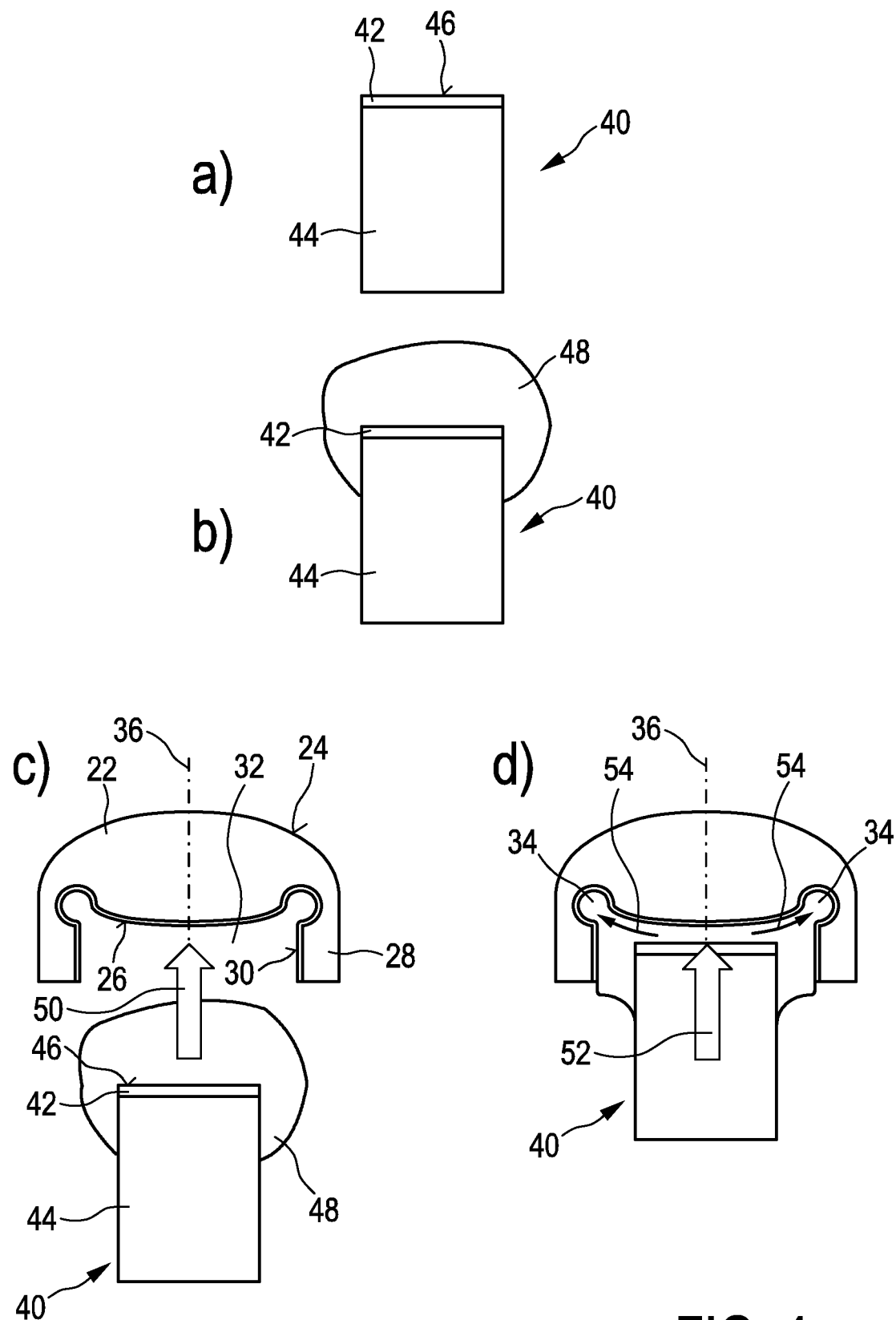
FIG. 4 shows single steps for connecting an ultrasound transducer to an acoustical lens shown in FIG. 2 in order to form the ultrasound probe shown in FIG. 3.

The upper portion of the support portion 40 including the transducer element 42 or the transducer array 42 is coated with the glue 48 by means of dip-coating or spray-coating as shown in FIG. 4b.

As shown in FIG. 4c, the ultrasound transducer 40 and the attached glue 48 are introduced into the cavity 32 as indicated by an arrow 50. The ultrasound transducer 40 is introduced into the cavity 32 so that the emission surface 46 faces the inner surface 26 and that the ultrasound transducer 40 is introduced coaxially to the axis of symmetry 36 into the cavity 32. When the emission surface 46 is introduced into the cavity 32 and still disposed in a distance to the inner surface 26, the ultrasound transducer 40 is pressed into the cavity 32 as shown in FIG. 4d by an arrow 52. In this certain step, the glue 48 disposed between the emission surface 46 and the inner surface 26 is moved or driven to the peripheral parts of the emission surface 46 and into the recesses 34 as shown by arrows 54. This is achieved by the convex curvature of the inner surface 26 so that the excessive glue 48 is driven into the recesses 34 including air bubbles so that finally the distance between the emission surface 46 and the inner surface 26 at the central part of the emission surface 26 is low and the air bubbles in the glue 48 are removed to the peripheral parts and in particular into the recesses 34. Hence, the reflections and the attenuation for the ultrasound waves in the central part of the emission surface 46 are reduced and the efficiency of the ultrasound wave emission of the probe 14 is improved.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an"

The invention claimed is:

1. Acoustical lens for an ultrasound probe, comprising:
an inner surface for facing an emission surface of an ultrasound transducer and for receiving ultrasound waves from the ultrasound transducer, wherein the inner surface is formed as a convexly curved surface;
an outer surface for emitting the ultrasound waves received at the inner surface;
one or more sidewalls forming a cavity with the inner surface, the cavity sized and shaped to receive the ultrasound transducer and a connection mold material between the ultrasound transducer and the convexly curved surface; and
at least one recess formed between the inner surface and the one or more sidewalls, the at least one recess configured for capturing air bubbles and excess connection mold material to reduce the amount of air bubbles between the ultrasound transducer and the convexly curved surface.

2. Acoustical lens as claimed in claim 1, wherein the inner surface is formed as a single convexly curved portion.

3. Acoustical lens as claimed in claim 1, wherein the at least one recess has a concave shape.

4. Acoustical lens as claimed in claim 1, wherein the at least one recess is formed as a notch surrounding the inner surface at least partially.

5. Acoustical lens as claimed in claim 1, wherein the at least one recess entirely surrounds the inner surface.

6. Acoustical lens as claimed in claim 5, wherein the at least one recess is formed as a notch separating the inner surface from the sidewalls.

7. Acoustical lens as claimed in claim 1, wherein the inner surface is covered by a coating forming a moisture barrier.

8. Acoustical lens as claimed in claim 7, wherein the sidewalls and a surface of the at least one recess are covered by the coating forming the moisture barrier.

9. Acoustical lens as claimed in claim 7, wherein the coating is formed as a metal layer.

10. Ultrasound transducer probe comprising:
an ultrasound transducer including an emission surface for emitting ultrasound waves, and
an acoustical lens having an inner surface for facing the emission surface of the ultrasound transducer and for receiving the ultrasound waves from the emission surface, and an outer surface for emitting the ultrasound waves received at the inner surface, wherein the inner surface is formed as a convexly curved surface, and wherein at least one recess is formed between the inner surface and one or more sidewalls, wherein the sidewalls and the inner surface form a cavity for receiving the ultrasound transducer and connection mold material, and wherein the at least one recess is configured for capturing air bubbles and excess connection mold material to reduce the amount of air bubbles between the ultrasound transducer and the convexly curved surface.

11. Ultrasound transducer probe as claimed in claim 10, wherein the emission surface is connected to the inner surface by means of the connection mold material.

12. Ultrasound transducer probe as claimed in claim 10, wherein the emission surface is a planar surface.

13. An ultrasound probe, comprising:
an ultrasound transducer comprising an emission surface configured to emit ultrasound waves;
an acoustic lens, comprising:
an inner surface, comprising:
a curved surface facing the emission surface of the ultrasound transducer and configured to receive the ultrasound waves from the emission surface;
a sidewall extending in a direction perpendicular to the emission surface of the ultrasound transducer, the sidewall and the curved surface forming a cavity in which the ultrasound transducer and connection mold material are disposed; and
a recess formed around at least a portion of the curved surface and configured for capturing air bubbles and excess connection mold material to reduce the amount of air bubbles between the emission surface and the curved surface; and
an outer surface configured emit the ultrasound waves received at the curved surface; and
the connection mold material disposed within the recess between the emission surface and the curved surface.

14. The ultrasound probe of claim 13, wherein the connection mold material comprises at least one of PDMS or polybutadiene.

15. The ultrasound probe of claim 13, wherein the curved surface includes a convexly curved portion.

16. The ultrasound probe of claim 13, wherein the recess completely surrounds the curved surface.

17. The ultrasound probe of claim 13, wherein the recess includes a concave surface.

18. The ultrasound probe of claim 13, wherein the connection mold material between the emission surface and the curved surface is free of air bubbles.

19. The ultrasound probe of claim 13, wherein the curved surface is positioned closer to the emission surface than the recess.

* * * * *